(12) United States Patent
Holmes

(10) Patent No.: US 11,308,751 B2
(45) Date of Patent: Apr. 19, 2022

(54) SYSTEM AND METHOD FOR DISPENSING ORDERS

(71) Applicant: RXSAFE LLC, Vista, CA (US)

(72) Inventor: William K. Holmes, San Diego, CA (US)

(73) Assignee: RXSAFE LLC, Vista, CA (US)

(*) Notice: Subject to any disclaimer, the term of this patent is extended or adjusted under 35 U.S.C. 154(b) by 0 days.

(21) Appl. No.: 16/955,365

(22) PCT Filed: Jan. 17, 2019

(86) PCT No.: PCT/US2019/014017
§ 371 (c)(1),
(2) Date: Jun. 18, 2020

(87) PCT Pub. No.: WO2019/143820
PCT Pub. Date: Jul. 25, 2019

(65) Prior Publication Data
US 2021/0142609 A1     May 13, 2021

Related U.S. Application Data

(60) Provisional application No. 62/618,245, filed on Jan. 17, 2018.

(51) Int. Cl.
*G16H 20/13* (2018.01)
*G07F 17/00* (2006.01)
(Continued)

(52) U.S. Cl.
CPC ........ *G07F 17/0092* (2013.01); *G07F 11/165* (2013.01); *G07F 11/1657* (2020.05);
(Continued)

(58) Field of Classification Search
CPC ....... G07F 17/0092; G07F 9/00; B65G 51/00; B65G 51/02; B65G 51/32; B65G 51/26; B65G 51/28
(Continued)

(56) References Cited

U.S. PATENT DOCUMENTS 2,207,434 A * 7/1940 Haven .................... B65G 51/40
406/70
4,146,195 A * 3/1979 Brooks .................. B65G 51/18
406/190
(Continued)

FOREIGN PATENT DOCUMENTS

RU         2 155 990 C2     9/2000
WO       2010 027717 A2     3/2010

OTHER PUBLICATIONS

International Search Report and Written Opinion for Application No. PCT/US2019/014017 dated May 15, 2019 (19 pages).
(Continued)

*Primary Examiner* — Timothy R Waggoner
(74) *Attorney, Agent, or Firm* — Michael Best & Friedrich LLP

(57) ABSTRACT

System and method for dispensing orders. One embodiment provides a method of dispensing a prescription order to a customer at a customer kiosk. The method includes receiving, at a pharmaceutical storage and retrieval device, an instruction to deliver a filled prescription to a customer kiosk and transferring, using a gantry assembly, the filled prescription to a chute connecting the pharmaceutical storage and retrieval device and a pneumatic delivery terminal. The method further includes opening a door of the pneumatic delivery terminal and operating an actuator to transfer the filled prescription from the chute to the pneumatic delivery terminal. The method also includes closing the door of the pneumatic delivery terminal and delivering, via a pneumatic tube, the filled prescription to the customer kiosk.

32 Claims, 16 Drawing Sheets

(51) Int. Cl.
  *G07F 11/16* (2006.01)
  *G07F 11/44* (2006.01)
  *G07F 11/62* (2006.01)
(52) U.S. Cl.
  CPC .............. *G07F 11/44* (2013.01); *G07F 11/62* (2013.01); *G16H 20/13* (2018.01)
(58) Field of Classification Search
  USPC ............................................ 700/218; 186/55
  See application file for complete search history.

(56) References Cited

U.S. PATENT DOCUMENTS

| | | | | |
|---|---|---|---|---|
| 4,993,882 | A * | 2/1991 | Nishizuka | ............... B65F 5/005 406/117 |
| 5,065,852 | A | 11/1991 | Marti | |
| 5,805,454 | A * | 9/1998 | Valerino, Sr. | .......... B65G 51/34 700/215 |
| 5,816,443 | A * | 10/1998 | Bustos | .................... E04H 14/00 221/211 |
| 6,164,491 | A * | 12/2000 | Bustos | ..................... G07F 7/00 221/211 |
| 6,286,714 | B1 | 9/2001 | Pearson et al. | |
| 6,711,460 | B1 | 3/2004 | Reese | |
| 7,630,788 | B1 | 12/2009 | Reese | |
| 8,849,445 | B2 | 9/2014 | Holmes | |
| 2001/0056311 | A1* | 12/2001 | Valerino, Sr. | .......... B65G 51/40 700/214 |
| 2005/0049746 | A1* | 3/2005 | Rosenblum | ............ G16H 20/13 700/232 |
| 2010/0100226 | A1 | 4/2010 | Valerino, Sr. | |
| 2019/0183737 | A1* | 6/2019 | Valerino, Sr. | ........ A61G 7/0506 |

OTHER PUBLICATIONS

Extended Search Report issued from the European Patent Office for related Application No. 19740739.8 dated Sep. 24, 2021 (9 Pages).

* cited by examiner

SYSTEM AND METHOD FOR DISPENSING ORDERS

CROSS-REFERENCE TO RELATED APPLICATIONS

This application claims priority to U.S. Provisional Patent Application No. 62/618,245, filed Jan. 17, 2018, the entire contents of which are incorporated by reference herein.

FIELD OF THE INVENTION

The present invention relates to systems and methods for dispensing orders. More particularly, the present invention relates to systems and methods for dispensing prescription orders in a retail setting, such as a pharmacy.

SUMMARY

In one embodiment, the invention provides a system for dispensing a prescription order to a customer. The system includes a storage and retrieval device having boxes that store prescription orders. The system also includes a kiosk connected to the pharmaceutical storage and retrieval device by a pneumatic tube. The pharmaceutical storage and retrieval device dispenses one of the prescription orders to the kiosk when the one of the prescription orders is claimed by the customer.

In another embodiment, the invention provides a method of dispensing a prescription order to a customer. The method includes storing prescription orders in a storage and retrieval device, claiming one of the prescription orders at a remote kiosk, and directing the claimed prescription order from the pharmaceutical storage and retrieval device to the remote kiosk through a pneumatic tube.

In another embodiment, the invention provides a method of dispensing a prescription order to a customer at a customer kiosk. The method includes receiving, at a pharmaceutical storage and retrieval device, an instruction to deliver a filled prescription to a customer kiosk and transferring, using a gantry assembly, the filled prescription to a chute connecting the pharmaceutical storage and retrieval device and a pneumatic delivery terminal. The method further includes opening a door of the pneumatic delivery terminal and operating an actuator to transfer the filled prescription from the chute to the pneumatic delivery terminal. The method also includes closing the door of the pneumatic delivery terminal and delivering, via a pneumatic tube, the filled prescription to the customer kiosk.

Another embodiment provides a pharmaceutical storage and retrieval device including a housing, a storage area in the housing for storing filled prescriptions, an outlet on the housing, a gantry assembly in the housing configured to transport the filled prescriptions from the storage area to the outlet, and a chute connecting the outlet to a pneumatic delivery terminal. The chute includes a pushing member movable relative to the chute to deliver the filled prescriptions from the chute to the pneumatic delivery terminal and an actuator coupled to the pushing member and configured to move the pushing member.

Another embodiment provides a pharmacy dispensing system including a pharmaceutical storage and retrieval device inside a pharmacy. The pharmaceutical storage and retrieval device includes a first outlet and a second outlet. The pharmacy dispensing system also includes a first kiosk located inside the pharmacy, a second kiosk located outside the pharmacy, and a pneumatic delivery system connecting the pharmaceutical storage and retrieval device, the first kiosk, and the second kiosk. The pneumatic delivery system includes a first pneumatic delivery terminal coupled to the first outlet and a first pneumatic delivery conduit extending between the first pneumatic delivery terminal to the first kiosk. Filled prescriptions are delivered from the first outlet to the first kiosk through the first pneumatic delivery terminal and the first pneumatic delivery conduit. The pneumatic delivery system also includes a second pneumatic delivery terminal coupled to the second outlet and a second pneumatic delivery conduit extending between the second pneumatic delivery terminal to the second kiosk. Filled prescriptions are delivered from the second outlet to the second kiosk through the second pneumatic delivery terminal and the second pneumatic delivery conduit.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In a retail location, such as a pharmacy, it is desirable to dispense or distribute items, such as prescription orders, to customers in an efficient manner. The present invention relates to systems and methods for dispensing prescription orders from a secure, bulk-storage machine to a plurality of different locations inside and outside a pharmacy.

Figure 1:
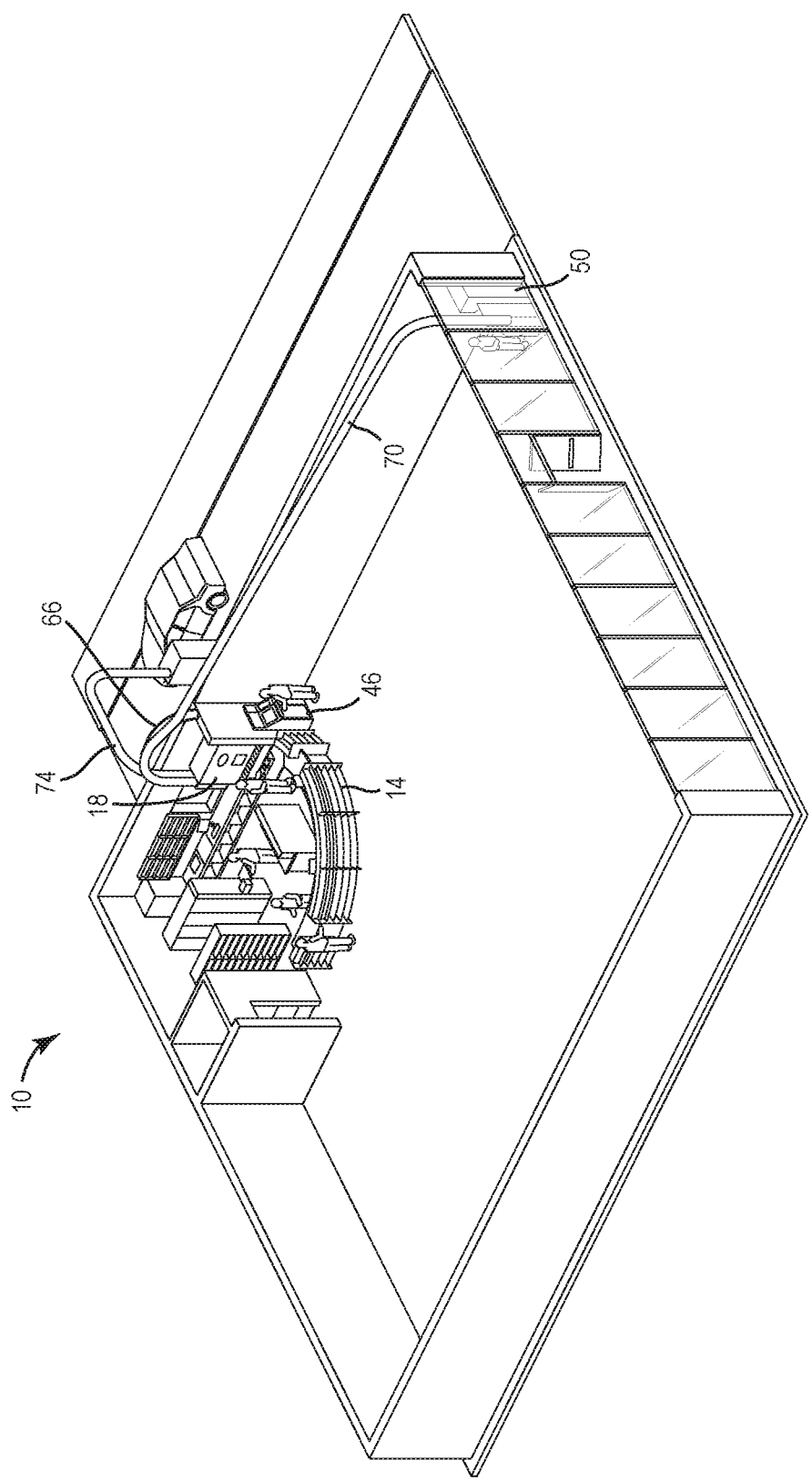
FIG. 1 is a perspective view of a pharmacy including a system for dispensing prescription orders to customers.
Figure 2:
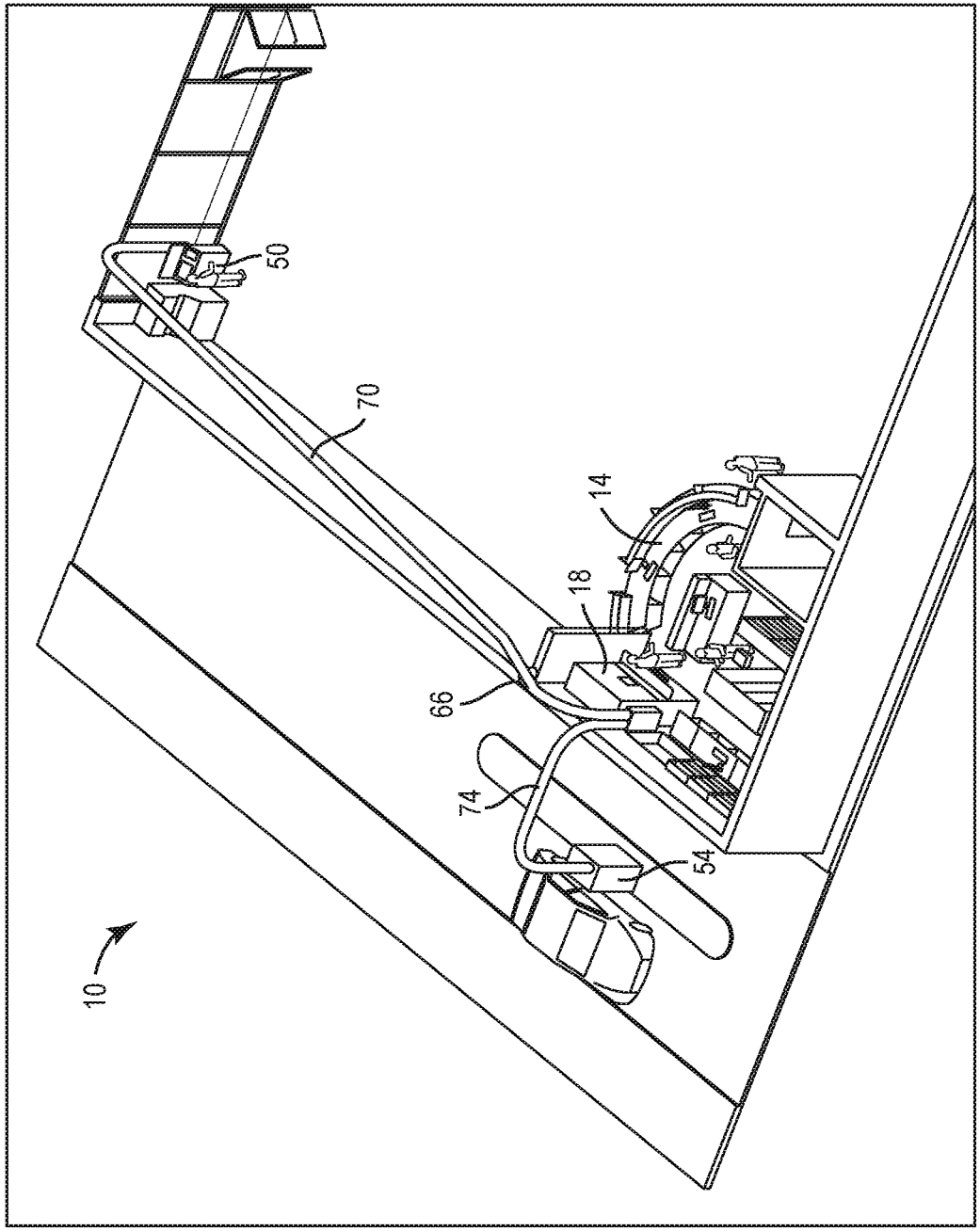
FIG. 2 is another perspective view of the pharmacy.

FIGS. 1 and 2 illustrate a retail location, or store, such as a pharmacy 10. The illustrated pharmacy 10 is part of a larger building, but may alternatively be a standalone pharmacy. The pharmacy 10 includes a counter 14, walls, and other structures that separate pharmacists and other technicians working in the pharmacy 10 from customers in the retail location. Behind the counter 14 are various machines for storing pharmaceuticals, prescriptions, and other controlled substances.

Figure 3:
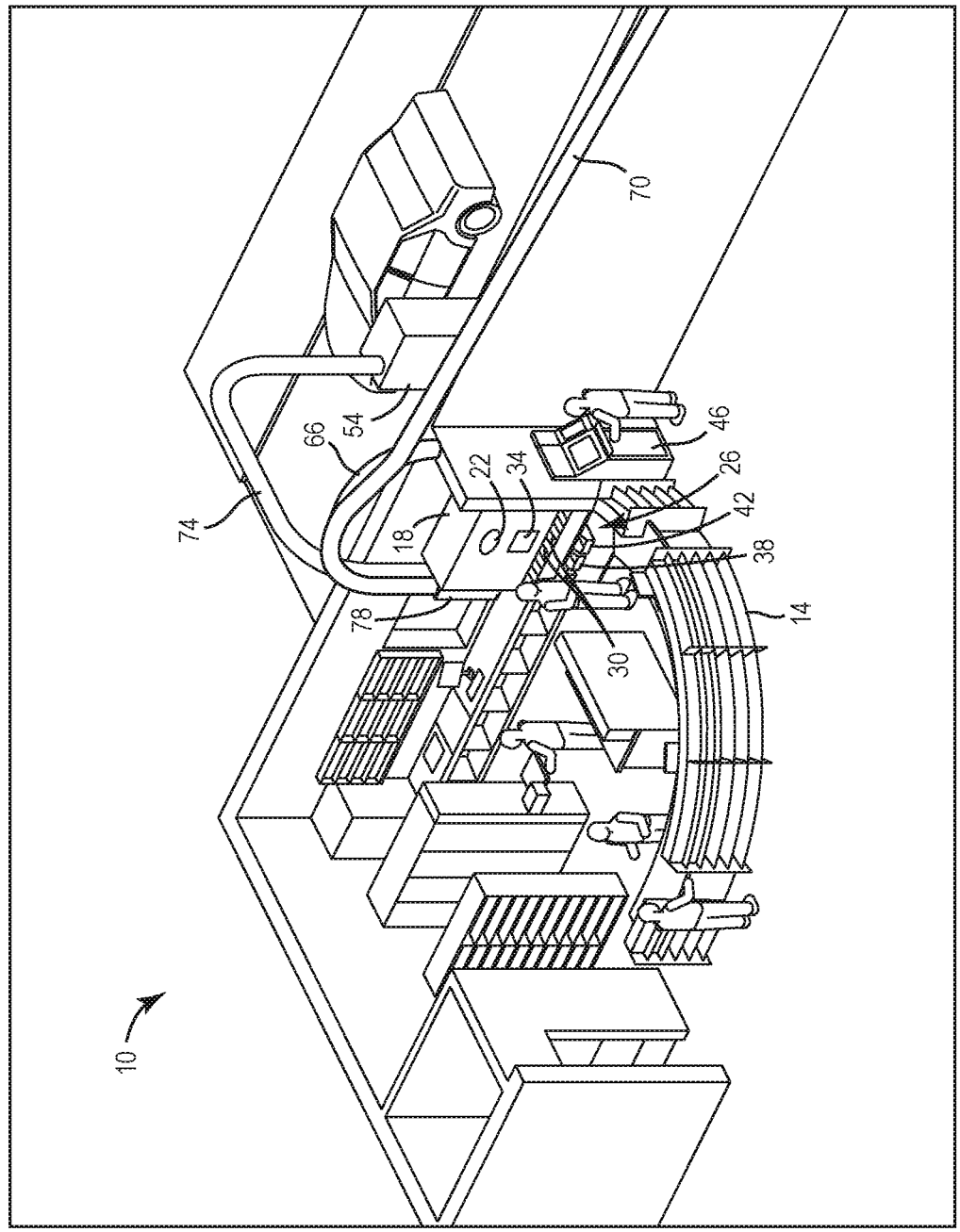
FIG. 3 is an enlarged perspective view of a portion of the pharmacy.
Figure 4:
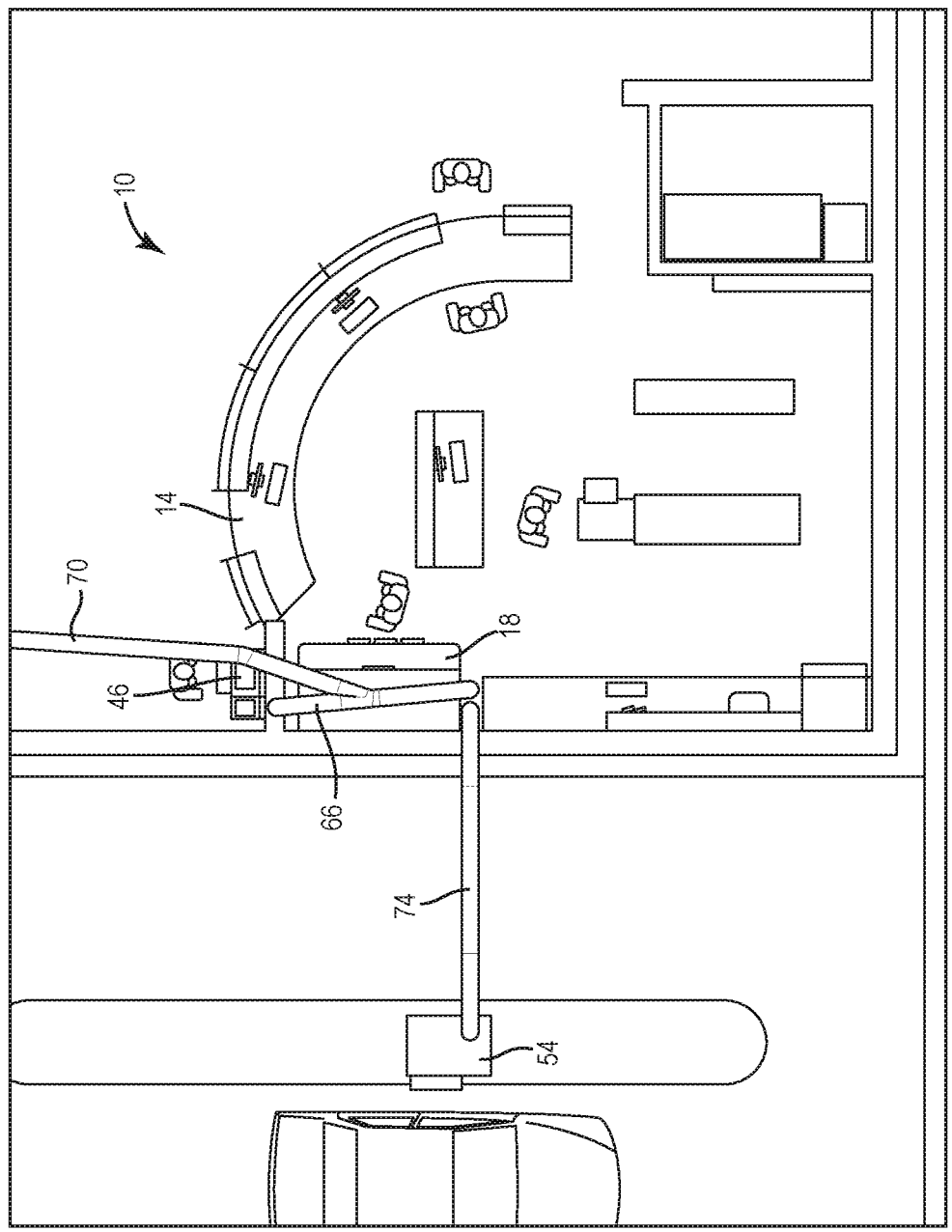
FIG. 4 is a top view of the portion of the pharmacy shown in FIG. 3.
Figure 5:
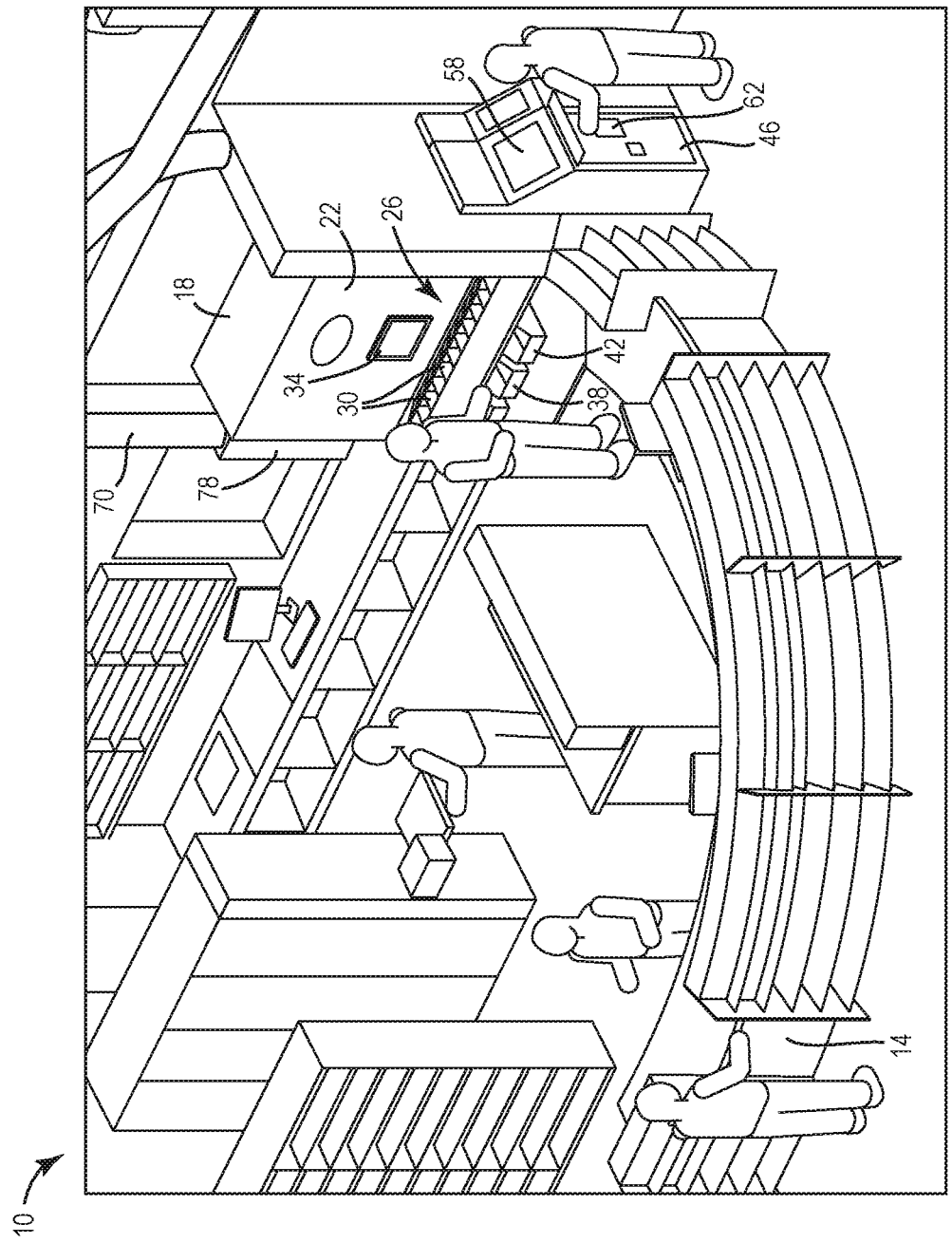
FIG. 5 is another enlarged perspective view of the portion of the pharmacy shown in FIG. 3.

As shown in FIGS. 3-5, the pharmacy 10 includes a pharmaceutical storage and retrieval device 18. The pharmaceutical storage and retrieval device 18 is similar to the pharmaceutical storage and retrieval system disclosed in U.S. Pat. No. 8,849,445, the entire contents of which are incorporated by reference herein. The illustrated device 18 includes a housing 22, an interior storage area, and a staging area 26. A plurality of containers or boxes 30 are stored within the interior storage area. The boxes 30 are moved between the storage area and the staging area 26 by a gantry assembly 90. When the boxes 30 are positioned in the storage area, the boxes 30 may be opened by a pharmacist or technician and filled with a prescription order. In the illustrated embodiment, each box 30 is configured to hold one prescription order, and each prescription order is separately bagged and tagged. As the prescription orders are loaded into the boxes 30, the prescription orders are scanned (e.g., by a scanner mounted to the housing 22 adjacent the staging area 26) to track which box 30 has which prescription order. The filled box 30 is then moved from the staging area 26 by the gantry assembly 90 to a location within the interior storage area.

The illustrated staging area 26 allows multiple, empty boxes 30 to be readily available to a pharmacist or technician at any time. In the illustrated embodiment, twelve boxes are arranged in a row in the staging area 26 to receive prescription orders. In other embodiments, the staging area 26 may be configured (e.g., sized) to simultaneously support fewer or more than twelve boxes. By providing multiple boxes 30 in the staging area 26, a pharmacist or technician can quickly load multiple prescription orders into the boxes 30 (with one prescription order going into each box 30). In other words, the pharmacist or technician does not have to wait for the gantry assembly 90 to move each box 30 to the staging area 26 one at a time. Rather, as each box 30 is filled, the gantry assembly 90 can automatically grab the box 30, move the box 30 to the storage area, and move an empty box 30 to the staging area 26. During this time, the pharmacist can continue working with and filling the other boxes 30 in the staging area 26. In some embodiments, the gantry assembly 90 may be triggered to grab a box 30 after the box 30 is opened, a prescription order is scanned, and the box 30 is reclosed. Alternatively, the gantry assembly 90 may be triggered to grab a box 30 when a pharmacist or technician confirms the box 30 is filled using a touchscreen 34 (or other input device) located on the front of the housing 22.

The interior storage area is a high-density storage area. In some embodiments, the storage area may receive and store more than 1000 boxes 30. The size of the interior storage area is dependent on the size of the housing 22. Different sized storage and retrieval devices may be used for different pharmacies, depending on the needs and volumes of sales of the pharmacies. As the boxes 30 are moved by the gantry assembly 90 into locations within the storage area, the pharmaceutical storage and retrieval device 18 tracks the locations of the boxes 30 so that the device 18 knows where each box 30 (and corresponding prescription order) is located. The device 18 includes an electronic processor and memory to control the gantry assembly 90 and store the location information. In some embodiments, the device 18 may also or alternatively include a network connection to communicate with a server having a server electronic processor and server memory that controls the gantry assembly 90 and/or stores the location information.

When a customer comes to claim his/her prescription order, the pharmaceutical storage and retrieval device 18 can dispense the claimed prescription order at the device 18. For example, a pharmacist or technician can input information regarding the claimed prescription order either into the touchscreen 34 on the housing 22 or into a pharmacy computer that communicates with the device 18. The gantry assembly 90 then retrieves the desired box 30 from the interior storage area, and empties the box 30 into a bin 38 mounted to the housing 22. The bin 38 is accessible to the pharmacist or technician to give the claimed prescription order to the customer. If a customer is claiming multiple prescription orders, all of the prescription orders may be emptied into the same bin 38 by the gantry assembly 90.

In some embodiments, the pharmaceutical storage and retrieval device 18 may include multiple bins 38. In such embodiments, each bin 38 may be assigned to a different pharmacist or technician. Each pharmacist or technician may only access his/her assigned bin 38 to retrieve certain prescription orders. Additionally, each bin 38 may be a secure bin that requires biometric information or a passcode to open.

In the illustrated embodiment, the pharmaceutical storage and retrieval device 18 also includes a return-to-stock bin 42. Prescription orders are emptied into this bin 42 if the orders are unclaimed after a set amount of time (e.g., fourteen days). Additionally, prescription orders can be emptied into this bin 42 if the pharmaceuticals in the order are going to expire or are being recalled. A pharmacist or technician can then retrieve the unclaimed, expired, or recalled prescription orders from the bin 42 and either return the pharmaceuticals to stock or dispose of the pharmaceuticals.

Figure 6:
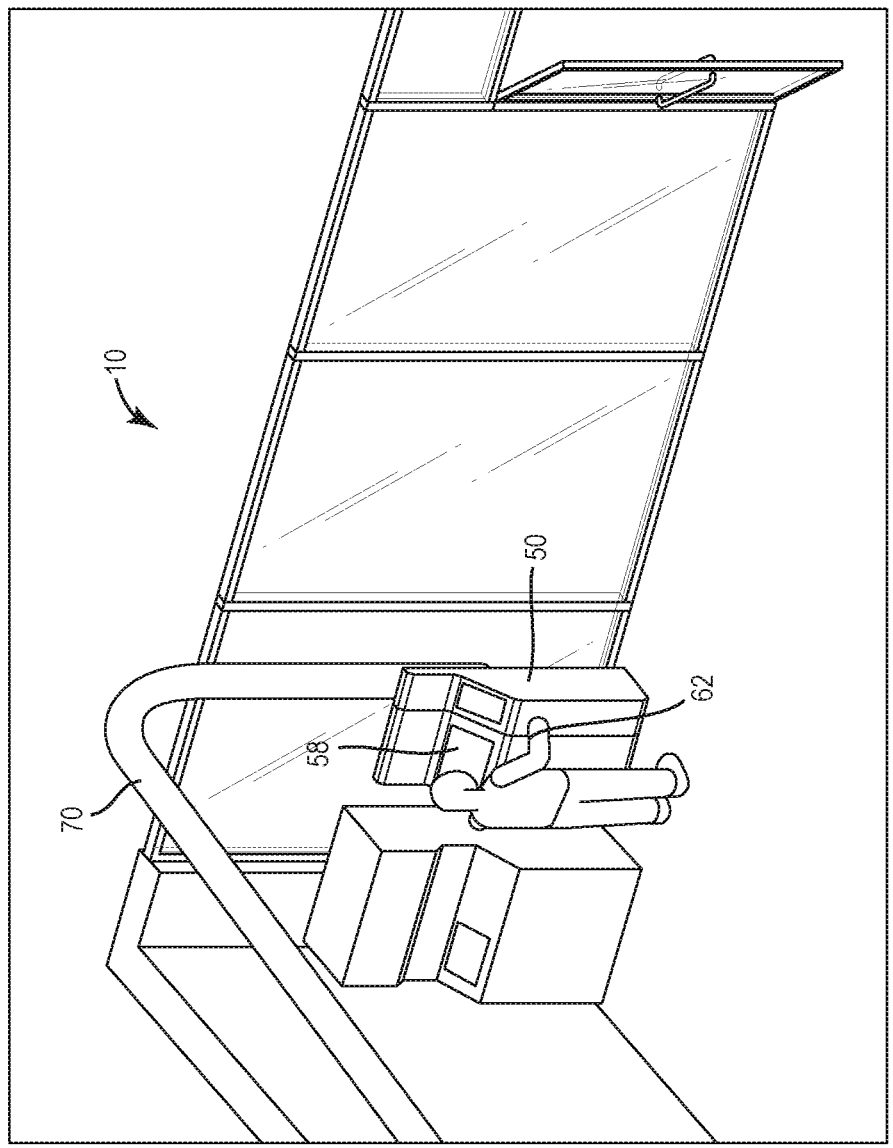
FIG. 6 is an enlarged perspective view of another portion of the pharmacy.
Figure 7:
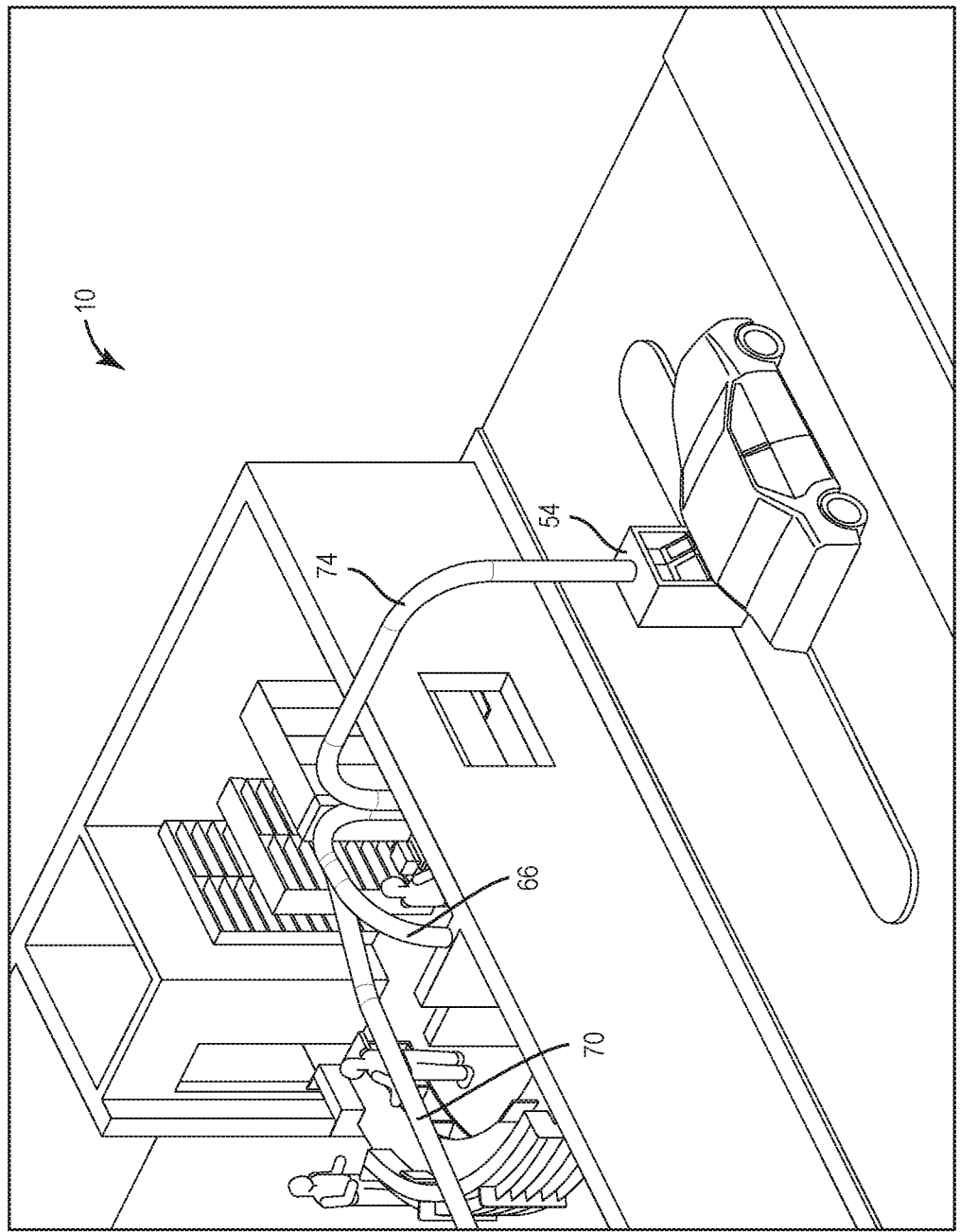
FIG. 7 is an enlarged perspective view of yet another portion of the pharmacy.

The pharmaceutical storage and retrieval device 18 also dispenses claimed prescription orders to more remote locations in the store. In the illustrated embodiment, the store includes a first self-serve kiosk 46 (FIG. 3) (for example, a first kiosk located inside the pharmacy 10) proximate the counter 14 of the pharmacy 10, a second self-serve kiosk 50 (FIG. 6) across the store from the pharmacy 10, and a third self-serve kiosk 54 (FIG. 7) (for example, a second kiosk located outside the pharmacy 10) outside the store. The pharmaceutical storage and retrieval device 18 and the self-service kiosks 46, 50, 54 form a pharmacy dispensing system. In some embodiments, the self-service kiosks 46, 50, 54 are self-service terminals sold by Diebold®. As shown in FIGS. 5 and 6, the kiosks 46, 50, 54 are modified to include an input/output device 58 and a payment system 62 suitable for use in the pharmacy. In the illustrated embodiment, the input/output device 58 is a touchscreen. A customer can navigate through the touchscreen 58 to claim his or her prescription order. The customer can then pay for the claimed prescription order using the payment system 62, which in some embodiments includes a credit card swipe and a signature pad.

In some embodiments, each kiosk 46, 50, 54 may also include a communication line, such as a phone line or network connection. The communication line communicates with the pharmaceutical storage and retrieval device 18 to request prescription orders. The communication line also allows the customer to communicate with a remote pharmacist. The customer can ask the remote pharmacist questions regarding his/her prescription, or ask for assistance in using the kiosk 46, 50, 54. The pharmacist can also verify that the correct person is claiming a particular prescription order. This may be particularly useful for the third kiosk 54 (FIG. 7) located outside the store. Each kiosk 46, 50, 54 may further include a camera and microphone that allows the customer to communicate with the pharmacist.

In the illustrated embodiment, the kiosks 46, 50, 54 are connected to the pharmaceutical storage and retrieval device 18 by pneumatic tubes 66, 70, 74, or conduits (for example, a first pneumatic delivery conduit and a second pneumatic delivery conduit). The pneumatic tubes 66, 70, 74 may be, for example, eight inch diameter tubes. The pneumatic tubes 66, 70, 74 use air pressure to move prescription orders from the pharmaceutical storage and retrieval device 18 to each kiosk 46, 50, 54. One tube 66, 70, 74 is associated with each kiosk 46, 50, 54. The tubes 66, 70, 74 are configured to extend up to 200 feet away from the pharmaceutical storage and retrieval device 18. Although the illustrated tubes 66, 70, 74 are visible in the figures as extending through walls and across the pharmacy 10, it should be readily apparent that the tubes 66, 70, 74 can be hidden within the walls or the ceiling of the pharmacy 10.

As shown in FIG. 5, the pneumatic tubes 66, 70, 74 are connected to an outlet 78 of the pharmaceutical storage and retrieval device 18. In the illustrated embodiment, the outlet 78 is mounted to a side of the housing 22. Each tube 66, 70, 74 extends from an upper surface of the outlet 78. The outlet 78 is accessible to the gantry assembly 90 positioned within the interior storage area. When a particular prescription order is requested by one of the kiosks 46, 50, 54, the gantry assembly 90 moves the box 30 containing that prescription order to the outlet 78. The gantry assembly 90 (or a separate robotic mechanism at the outlet 78) then opens the box 30, takes the prescription order out of the box 30, and loads the prescription order into the corresponding tube 66, 70, 74. In some embodiments, the gantry assembly 90 can load the prescription order into the corresponding tube 66, 70, 74 by rotating the box 30 and letting the prescription order fall into an opening associated with the tube 66, 70, 74. In other embodiments, the prescription order is moved to the corresponding tube 66, 70, 74 by a robotic gripper.

The above-described system improves a customer's experience in purchasing and obtaining his/her prescription orders. For example, the remote kiosks 46, 50, 54 allow a customer to pick-up prescription orders without waiting in line at the counter 14 of the pharmacy 10 for a pharmacist to become available. In addition, the third kiosk 54 located outside of the pharmacy 10 allows a customer to pick-up orders after hours. Most states require pharmaceuticals to be stored within a licensed pharmacy. By connecting the third kiosk 54 to the pharmaceutical storage and retrieval device 18 by the pneumatic tube 74, the pharmaceuticals remain within the walls of the pharmacy 10 until the pharmaceuticals are claimed by a customer.

The system also allows a customer to claim all or part of his/her order. For example, a customer may have an order that includes three different types of pharmaceuticals. Each pharmaceutical is packaged and labeled in a separate bag. Each bag is then stored by the pharmaceutical storage and retrieval device 18 in a separate box 30. When the customer comes to claim the order, he/she can decide whether to claim all three prescription orders, only two of the orders, or only one of the orders. Because the pharmaceuticals are not all bagged and stored in the same box 30 within the pharmaceutical storage and retrieval device 18, the orders do not need to be taken apart and repackaged if the customer claims less than the entire order.

In addition, the system improves storage of prescription orders for the pharmacy. Rather than requiring each kiosk 46, 50, 54 to hold a high volume of pharmaceuticals, or requiring a pharmacist or technician to manually walk and load prescription orders out to each kiosk 46, 50, 54, all of the prescription orders can be stored in the pharmaceutical storage and retrieval device 18. Since the pharmaceutical storage and retrieval device 18 is a high-volume storage unit, the pharmacy 10 can store as many prescription orders as needed. As noted above, storing the prescription orders within the pharmaceutical storage and retrieval device 18 also ensures that all of the pharmaceuticals remain within the licensed pharmacy until claimed.

Furthermore, the pharmaceutical storage and retrieval device 18 is an automated machine that allows a pharmacist, technician, or manager to make adjustments to storage protocols. Typically, a prescription order is held by a pharmacy for up to fourteen days. After fourteen days, the prescription order is returned to stock if unclaimed. If the pharmacist, technician, or manager knows a busy time of year is coming up (e.g., around the holidays) and would like a higher turnover of prescription orders in the device 18, the pharmacist, technician, or manager can set the device 18 to return prescription orders to stock after a shorter time period (e.g., ten days). This frees up more space within the pharmaceutical storage and retrieval device 18 for new prescription orders.

Figure 8:
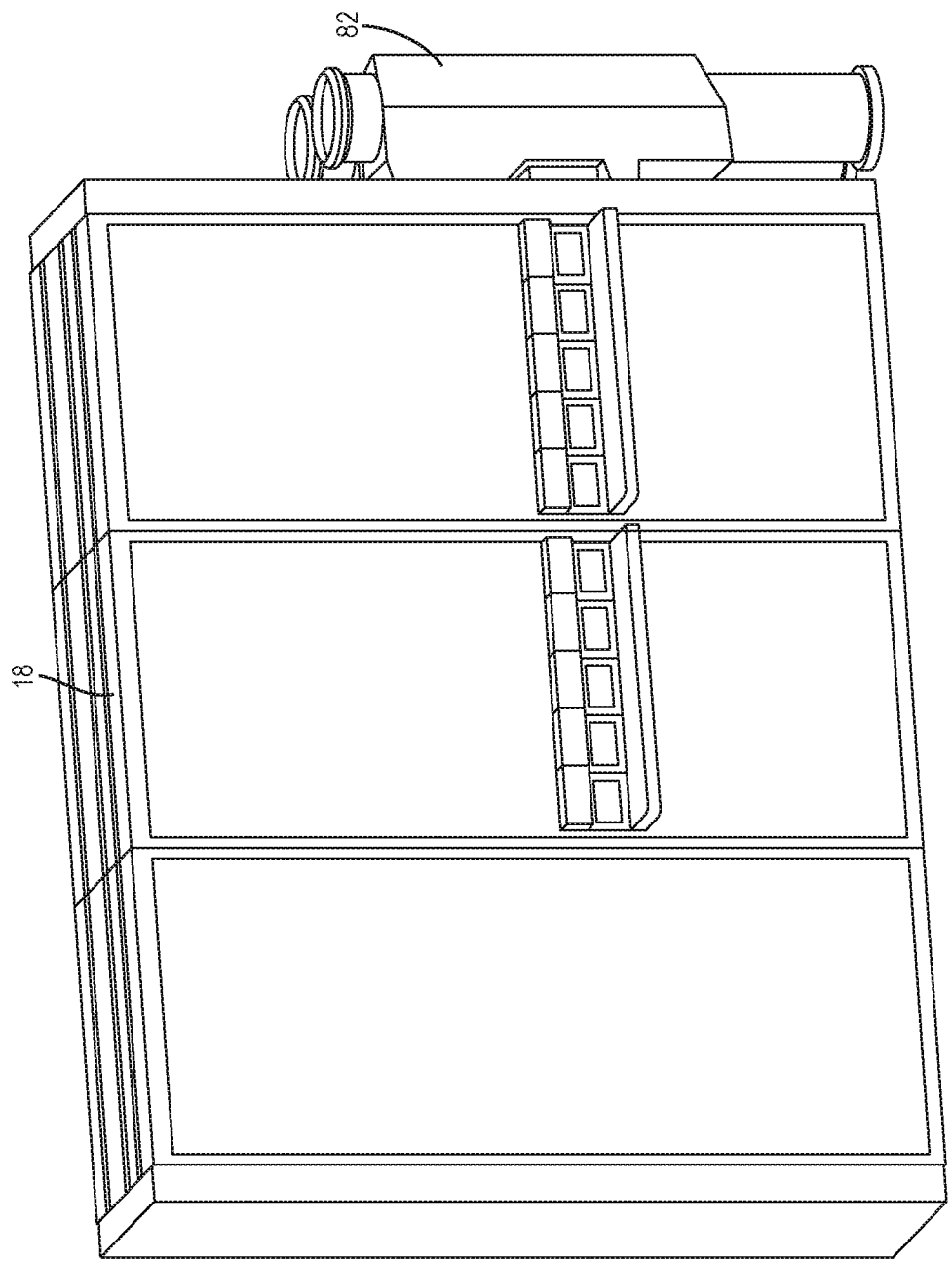
FIG. 8 is a perspective view of a connection between a pharmaceutical storage and retrieval device and a pneumatic delivery system.
Figure 9A:
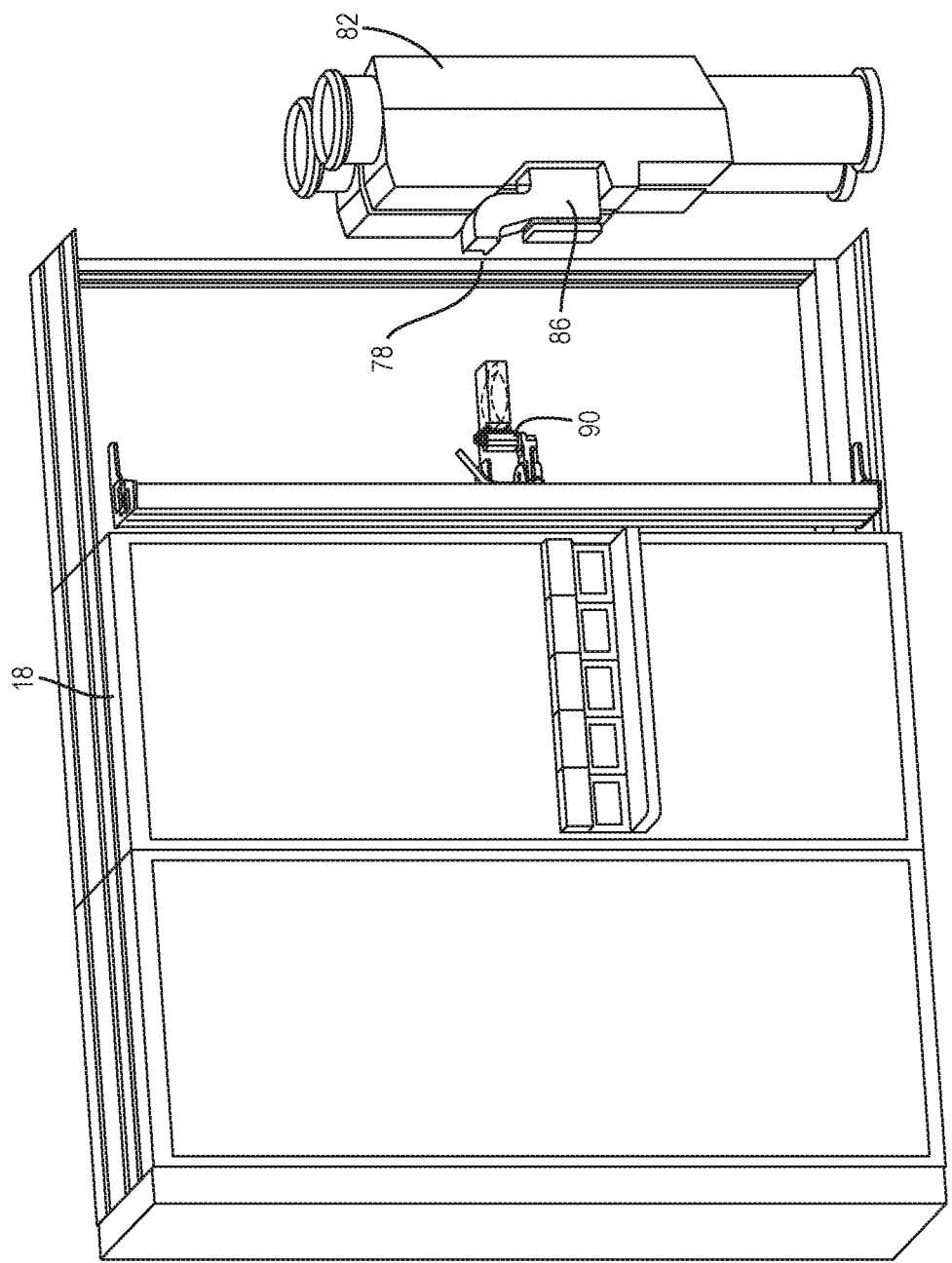
FIGS. 9A-9B are perspective views of a gantry assembly interacting with the pneumatic delivery system of FIG. 8.
Figure 9B:
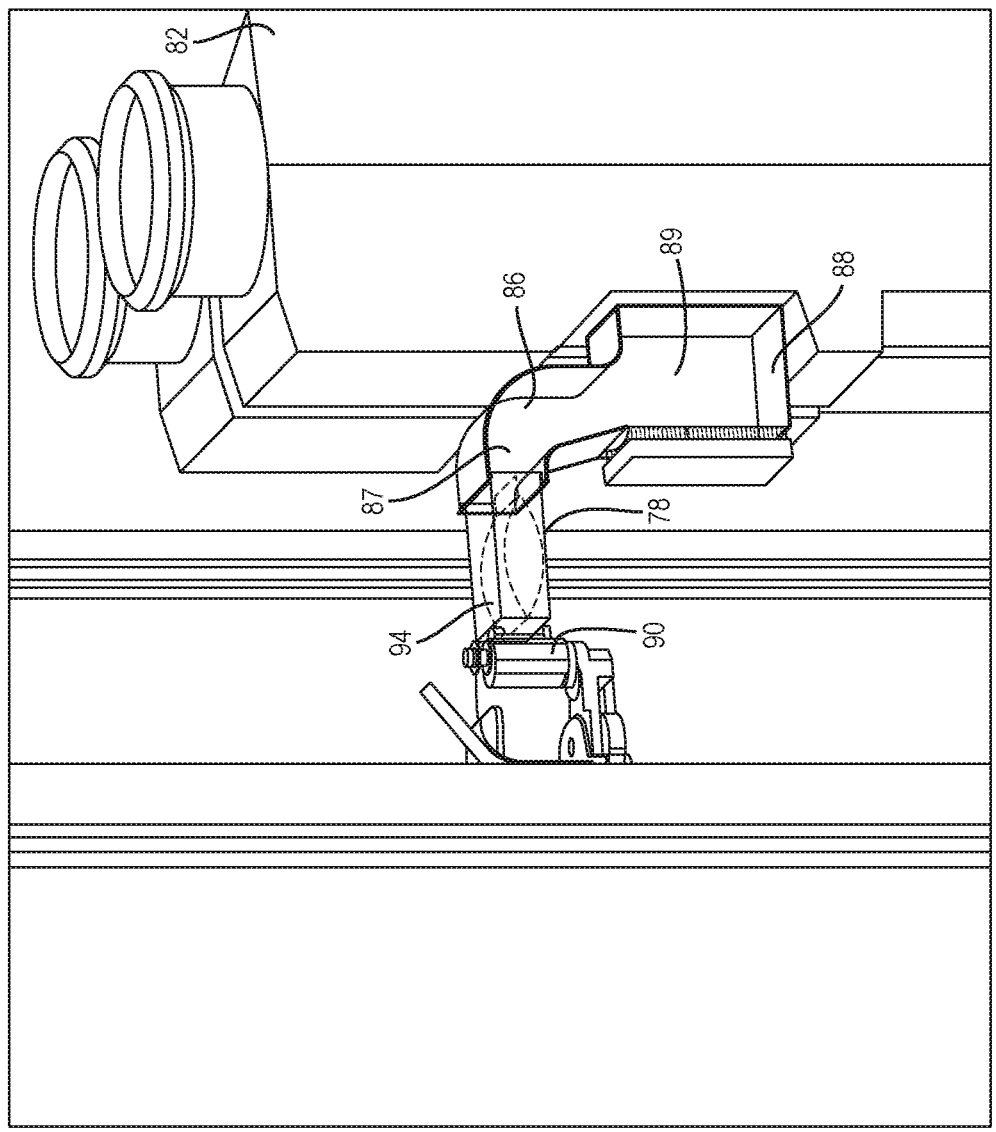
Figure 10A:
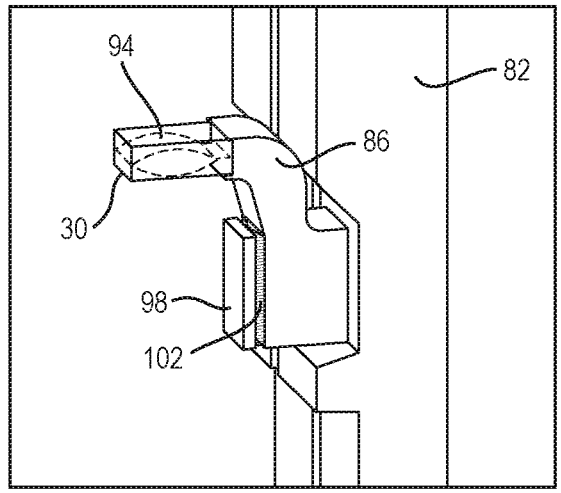
FIGS. 10A-10D illustrate the connection between the pharmaceutical storage and retrieval device and the pneumatic delivery system.
Figure 10B:
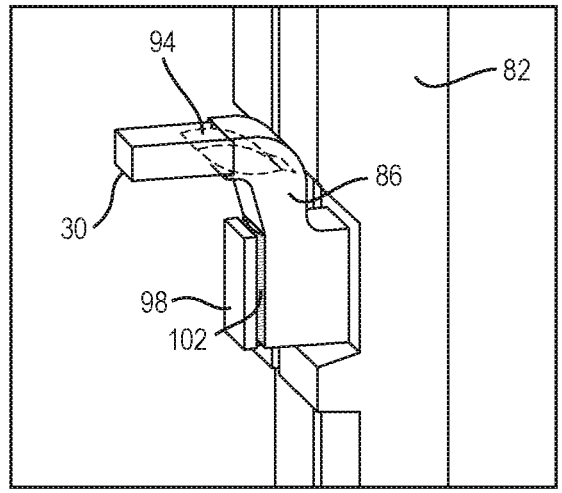
Figure 10C:
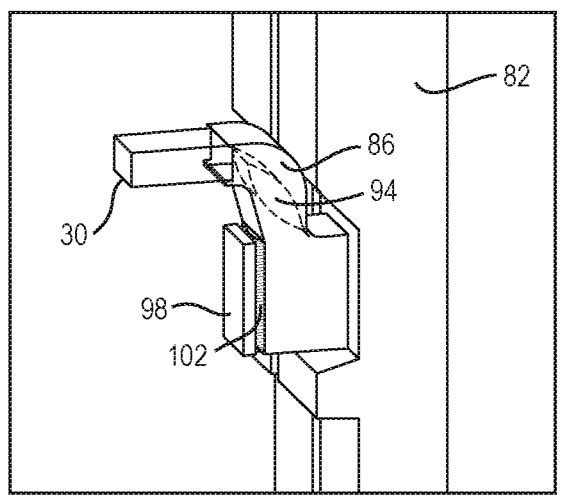
Figure 10D:
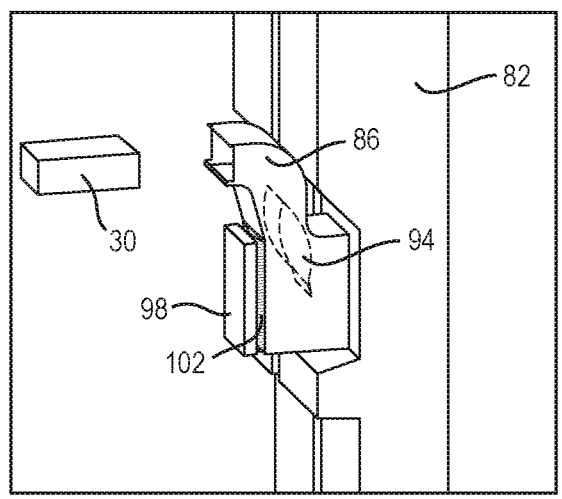

FIGS. 8-9B illustrate a connection between the pharmaceutical storage and retrieval device 18 and a pneumatic delivery terminal 82. The pharmacy 10 may include a separate pneumatic delivery terminal 82 to connect the pharmaceutical storage and retrieval device 18 to each one of the customer kiosks 46, 50, 54 (for example, a first pneumatic delivery terminal, and a second pneumatic delivery terminal). The pneumatic delivery terminals 82 and the pneumatic conduits 66, 70, 74 together form a pneumatic delivery system that connect the pharmaceutical storage and retrieval system to the customer kiosks 46, 50, 54. The pneumatic delivery terminal 82 is connected to the outlet 78 of the pharmaceutical storage and retrieval device 18 by a chute 86. The pharmaceutical storage and retrieval device 18 may include a separate outlet 78 (for example, a first outlet and a second outlet) corresponding to each one of the customer kiosks 46, 50, 54. As described above, the outlet 78 is accessible by the gantry assembly 90. The gantry assembly 90 delivers a filled prescription 94 stored in the pharmaceutical storage and retrieval device 18 to the outlet 78. In some embodiments, the pharmaceutical storage and retrieval device 18 and the pneumatic delivery terminal 82 may be communicatively coupled. As such, the pharmaceutical storage and retrieval device 18 may communicate instructions to the pneumatic delivery terminal 82.

The chute 86 includes a first portion 87, a second portion 88, and a third portion 89. The first portion 87 is at the top of the chute 86 and connects the chute 86 to the outlet 78 of the pharmaceutical storage and retrieval device 18. The second portion 88 is at the bottom of chute 86 and the third portion 89 connects the chute 86 to the pneumatic delivery terminal 82.

Figure 12:
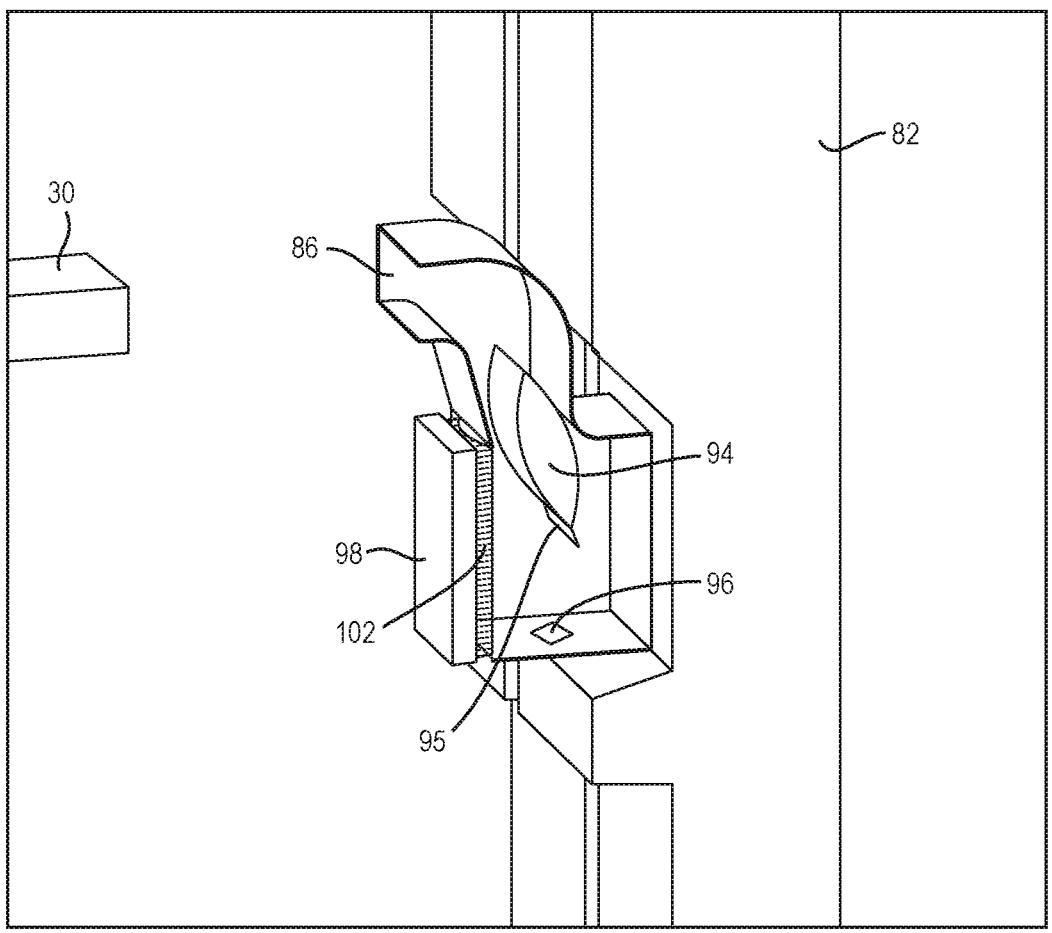
FIG. 12 illustrates the transfer mechanism between the pharmaceutical storage and retrieval device and the pneumatic delivery system.

FIGS. 10A-10D show the process of transferring a prescription from the outlet 78 to the pneumatic delivery terminal 82. When the gantry assembly 90 delivers the filled prescription 94 to the outlet 78, the filled prescription 94 falls from the first portion 87 through to the second portion 88 at the bottom of the chute 86. The chute 86 is connected with a slope to the outlet 78 such that when the filled prescription 94 is delivered to the chute 86, the filled prescription 94 falls to the bottom of the chute 86 due to gravity. That is, the chute 86 is sloped between the first portion 87 and the second portion 88. Several other methods may be used to transfer the filled prescription 94 to the bottom of the chute 86. For example, as shown in FIG. 12, the filled prescription 94 may be equipped with a magnet 95 (for example, a first magnet 95) (e.g., on a bag or container carrying the filled prescription). The chute 86 may then use another magnet 96 (for example, a second magnet 96 at the second portion 88) or create a magnetic field to move the filled prescription 94 to the bottom of the chute 86.

In some embodiments, more than one filled prescription 94 (for example, a plurality of filled prescriptions) may be transferred to the chute 86 for delivery to a customer kiosk 46, 50, 54. For example, more than one chute 86 (for example, a plurality of chutes 86) may be used to transfer filled prescriptions 94 between the pharmaceutical storage and retrieval device 18 and the pneumatic delivery terminal 82. The chutes 86 may be vertically or horizontally stacked and may be used to transfer multiple filled prescriptions 94 between the pharmaceutical storage and retrieval device 18 and the pneumatic delivery terminal 82. In some embodiments, a storage and retrieval device 18 may be connected to multiple pneumatic delivery terminals 82 with multiple chutes 86 positioned at different locations of the pharmaceutical storage and retrieval device 18.

Figure 16:
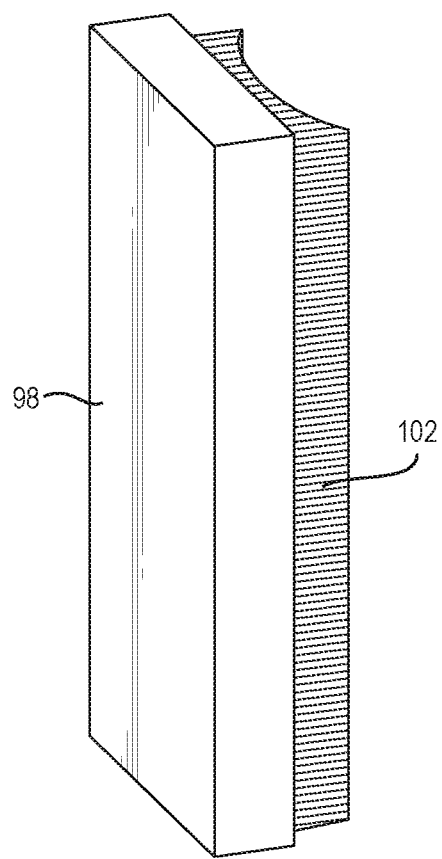
FIG. 16 is a perspective view of a pushing member of the transfer mechanism of FIG. 11.

The chute 86 includes a pushing member 98 to deliver the filled prescription 94 to the pneumatic delivery terminal 82. In the illustrated embodiment, the pushing member 98 includes a brush. The illustrated pushing member 98 also includes flexible bristles 102. In some embodiments, the bristles 102 include a concave front profile (as shown in FIG. 16). In other embodiments, the bristles 102 may have a different profile. The pushing member 98 may be operated by an actuator mechanism, for example, a motor and a ram as described below.

In some embodiments, to transfer more than one filled prescription 94, a first filled prescription 94 is first dropped into the chute 86. The pushing member 98 partially pushes the first filled prescription 94 and retracts to make space for a second filled prescription 94. When the second filled prescription 94 is dropped into the cute 86, the pushing member 98 may also partially push the second filled prescription 94 to make space for more filled prescriptions 94 until a desired number of filled prescriptions 94 are dropped into the chute 86. The pushing member 98 then transfers the plurality of filled prescriptions 94 to the pneumatic delivery terminal 82 together.

Figure 11:
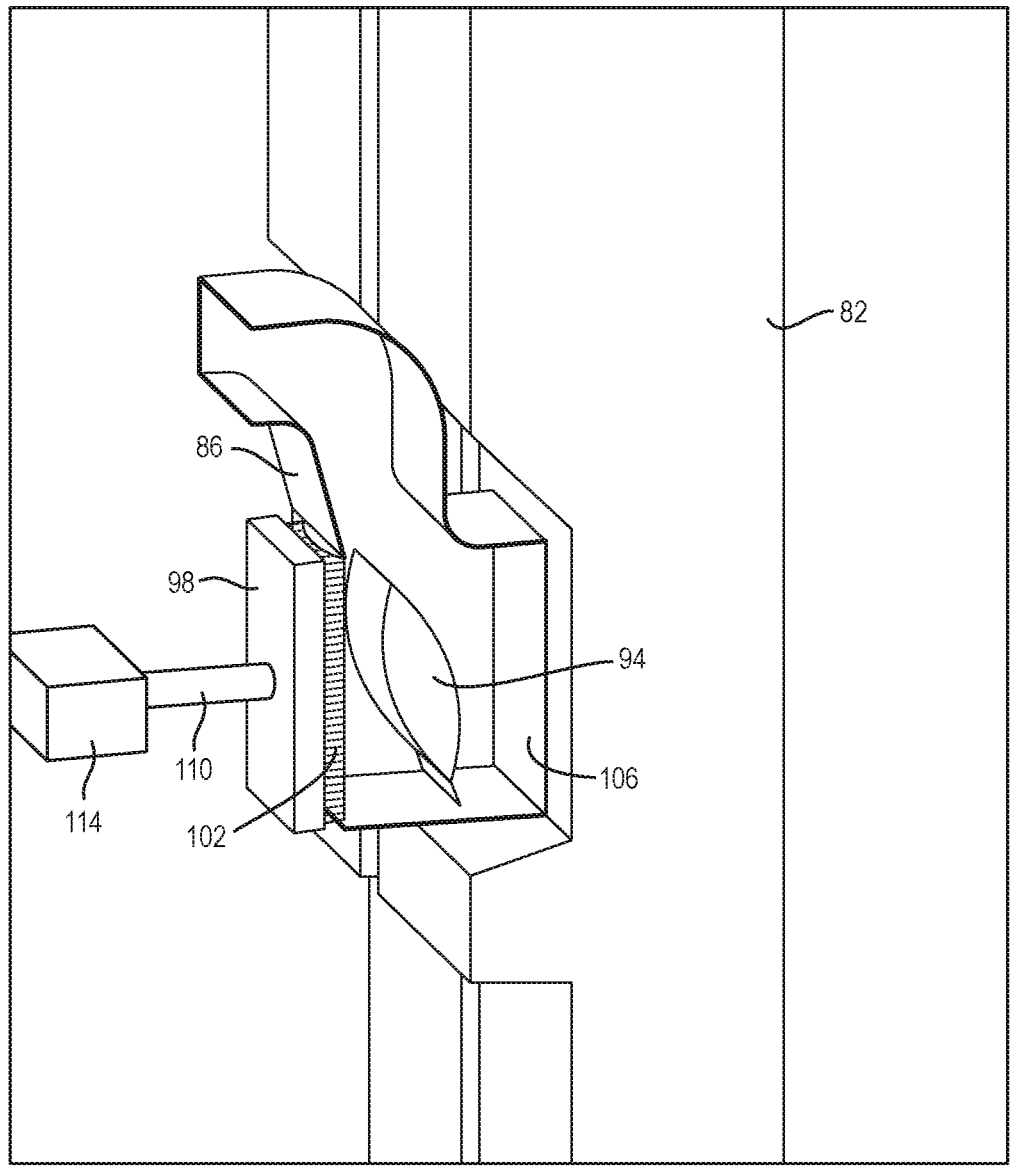
FIG. 11 illustrates a transfer mechanism between the pharmaceutical storage and retrieval device and the pneumatic delivery system.

FIG. 11 shows a sliding door 106 of the pneumatic delivery terminal 82. The sliding door 106, when open, allows the pushing member 98 to transfer the filled prescription 94 to the inside of the pneumatic delivery terminal 82. For example, as shown in FIGS. 12A-12C, when the sliding door 106 opens, the pushing member 98 pushes the filled prescription 94 to the inside of the pneumatic delivery terminal 82. The filled prescription 94 may be transferred to a container within the pneumatic delivery terminal 82. The container 94 including the filled prescription 94 is then transferred to the kiosks 46, 50, 54. In some embodiments, rather than a sliding door 106, the door 106 may include different types of doors, for example, a pivotable door 106 and the like.

FIG. 11 also shows an example actuator mechanism used to actuate the pushing member 98. The actuator mechanism includes a ram 110 coupled to the pushing member 98. The ram 110 is driven by a motor 114 to push the filled prescription 94 into the pneumatic delivery terminal 82. The ram 110 is, for example, a spring loaded hydraulic ram, a telescoping sliding tool, or the like. The motor 114 is, for example, a solenoid, a DC motor, or the like. The motor 114 may be electrically connected to the electronic processor of the pharmaceutical storage and retrieval device 18. The electronic processor may operate the motor 114 in response to, for example, detecting that a filled prescription 94 has been deposited in the chute 86. In some embodiments, other actuator mechanisms such as a solenoid spring and the like may be used to actuate the pushing member 98.

Figure 13A:
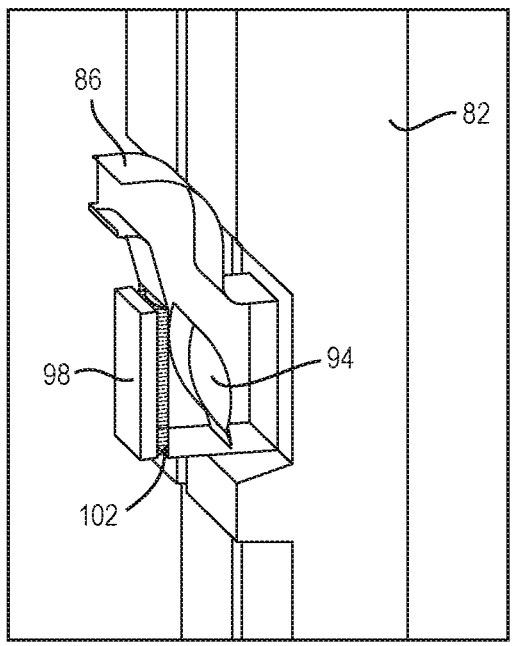
FIGS. 13A-13D illustrate a process of dispensing an order to the pneumatic delivery system of FIG. 8.

The pushing member 98 may be shaped such that the pushing member 98 substantially covers the opening in the pneumatic delivery terminal 82. Substantially covering the opening of the pneumatic delivery terminal 82 includes, for example, completely covering the opening in the pneumatic delivery terminal 82 with possibly a small gap around the perimeter. When the filled prescription 94 is delivered to the pneumatic delivery terminal 82, the sliding door 106 is closed while the pushing member 98 is still covering the opening to the pneumatic delivery terminal 82 (as shown in FIG. 13C). The flexible bristles 102 allow the sliding door 106 to be closed while the pushing member 98 is still covering the opening of the pneumatic delivery terminal 82. When the sliding door 106 is closed, the flexible bristles 102 deflect out of the way of the sliding door 106. However, because the bristles 102 are flexible, the bristles 102 do not hinder the operation of the sliding door 106. After the sliding door 106 is closed, the motor 114 controlling the ram 110 is operated to pull the pushing member 98 back to its original position (as shown in FIG. 13D).

The filled prescriptions 94 may have odd or irregular shapes. In some embodiments, it may be desirable to push the filled prescriptions 94 completely into the pneumatic delivery terminal 82 and past the sliding door 106 such that the filled prescriptions 94 are not caught in the sliding door 106 when the sliding door 106 is closed. In addition, it may also be desirable to ensure that the filled prescriptions 94 do not fall backwards into the chute 86 when the sliding door 106 is closed. Accordingly, the pushing member 98 and the flexible bristles 102 ensure both that the filled prescriptions 94 are pushed completely into the pneumatic delivery terminal 82 and that the filled prescriptions do not fall backwards when the sliding door 106 is closed. As described above, when the sliding door 106 is closed, the flexible bristles 102 are moved away (e.g., deflect) from the sliding door 106 and not trapped in the sliding door 106.

In some embodiments, to transfer more than one filled prescription 94, a first prescription 94 may be first dropped into the chute 86. The pushing member 98 transfers the first filled prescription 94 to the pneumatic delivery terminal 82 as described above. The pushing member 98 is then retracted to its original position before dropping a second filled prescription 94 into the chute 86. The pushing member 98 then pushes the second filled prescription 94 as close to the sliding door 106 as possible before the sliding door 106 is opened. For example, the second filled prescription 94 may be pushed such that the second filled prescription 94 is touching the sliding door 106. The sliding door 106 is then opened to transfer the second filled prescription 94 into the pneumatic delivery terminal 82. This ensures that the first prescription 94 does not fall backward when the sliding door 106 is opened to transfer the second filled prescription 94.

Figure 14:
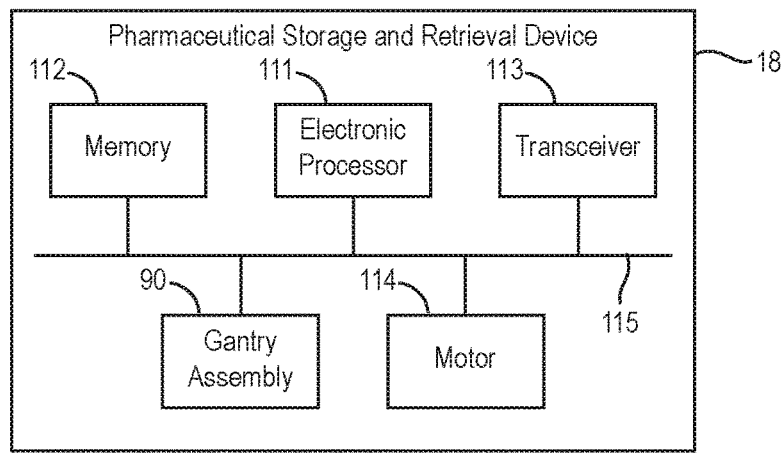
FIG. 14 is a block diagram of the pharmaceutical storage and retrieval device of FIG. 8.

FIG. 14 is a block diagram of one example embodiment of the pharmaceutical storage and retrieval device 18. In the example illustrated, the pharmaceutical storage and retrieval device 18 includes an electronic processor 111, a memory 112, a transceiver 113, the motor 114, and the gantry assembly 90. The electronic processor 111, the memory 112, the transceiver 113, the motor 114, and the gantry assembly 90 communicate over one or more control and/or data buses 115. In some embodiments, the electronic processor 111 is implemented as a microprocessor with separate memory, such as the memory 112. In other embodiments, the electronic processor 111 may be implemented as a microcontroller (with memory 112 on the same chip). In other embodiments, the electronic processor 111 may be implemented using multiple processors. In addition, the electronic processor 111 may be implemented partially or entirely as, for example, a field-programmable gate array (FPGA), an applications specific integrated circuit (ASIC), and the like, and the memory 112 may not be needed or be modified accordingly. In the example illustrated, the memory 112 includes non-transitory, computer-readable memory that stores instructions that are received and executed by the electronic processor 111 to carry out the functionality of the pharmaceutical storage and retrieval device 18 described herein. The memory 112 may include, for example, a program storage area and a data storage area. The program storage area and the data storage area may include combinations of different types of memory, such as read-only memory and random-access memory.

The transceiver 113 enables wired or wireless communication between the electronic processor 111 and the self-serve kiosks 46, 50, 54. In some embodiments, rather than a transceiver 113 the pharmaceutical storage and retrieval device 18 may include separate transmitting and receiving components, for example, a transmitter and a receiver.

The electronic processor 111 controls the gantry assembly 90 to move or transport the filled prescriptions from the internal storage area of the pharmaceutical storage and retrieval device 18 to the chute 86. The electronic processor 111 also controls the motor 114 (or other actuating mechanisms) to operate the pushing member 98 to move the filled prescription from the chute 86 to the pneumatic delivery terminal 82.

Figure 15:
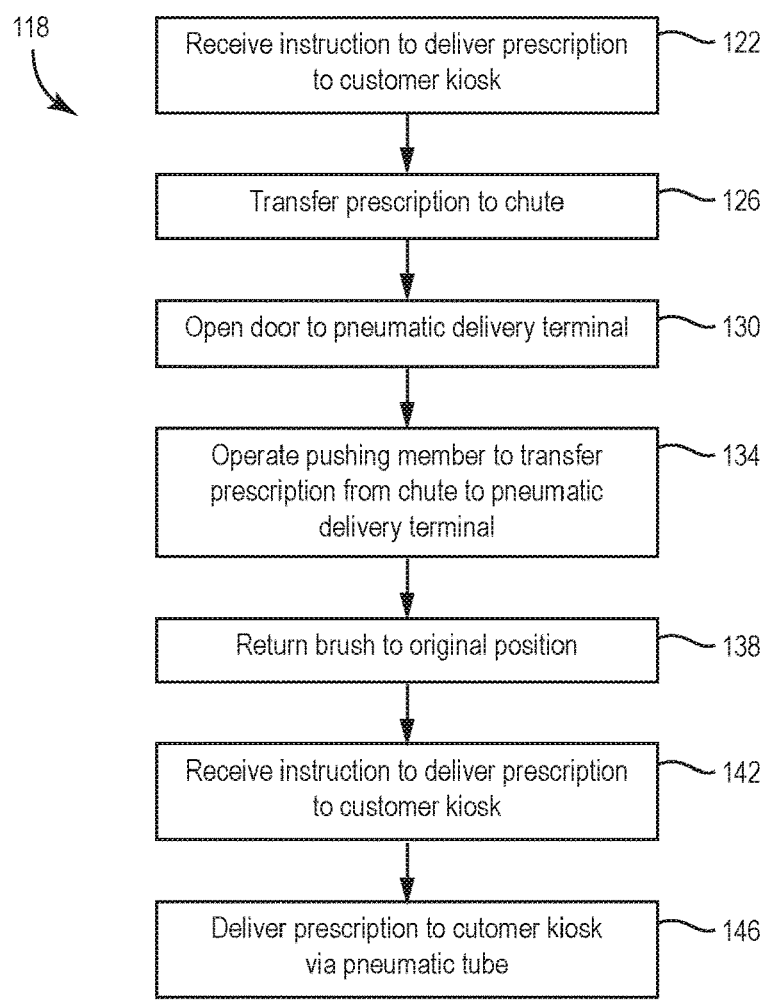
FIG. 15 is a flowchart illustrating a method of dispensing orders at a customer kiosk.

FIG. 15 is a flowchart depicting a method 118 for dispensing an order at a customer kiosk. The method 118 begins when the pharmaceutical storage and retrieval device 18 receives an instruction from one of the customer kiosks 46, 50, 54 (at step 122). For example, the electronic processor 111 receives the instruction from one of the customer kiosks 46, 50, 54 via the transceiver 113. The instruction may be received when a customer redeems a prescription at one of the kiosks 46, 50, 54. The kiosk 46, 50, 54 may verify information entered by the customer and communicate an instruction to deliver the prescription (for example, filled prescription 94) at the kiosk 46, 50, 54 where the customer entered the prescription information.

At step 126, the pharmaceutical storage and retrieval device 18 transfers the filled prescription 94 from the internal storage area of the pharmaceutical storage and retrieval device 18 to the chute 86 through the outlet 78. As described above, the electronic processor 111 controls the gantry assembly 90 of the pharmaceutical storage and retrieval device 18 to retrieve the filled prescription 94 from the inner storage area and transfer the filled prescription 94 to the chute 86. Once the filled prescription 94 is delivered to the chute 86, the filled prescription 94 rests at the bottom of the chute 86 in front of the pushing member 98 (see FIG. 13A).

Figure 13B:
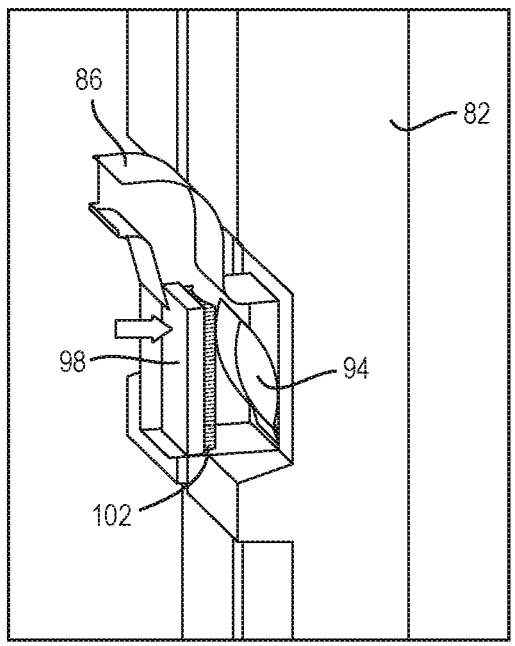
Figure 13C:
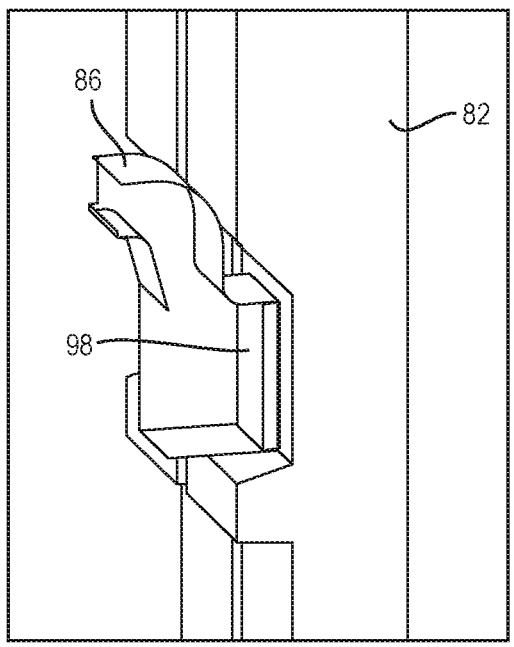
Figure 13D:
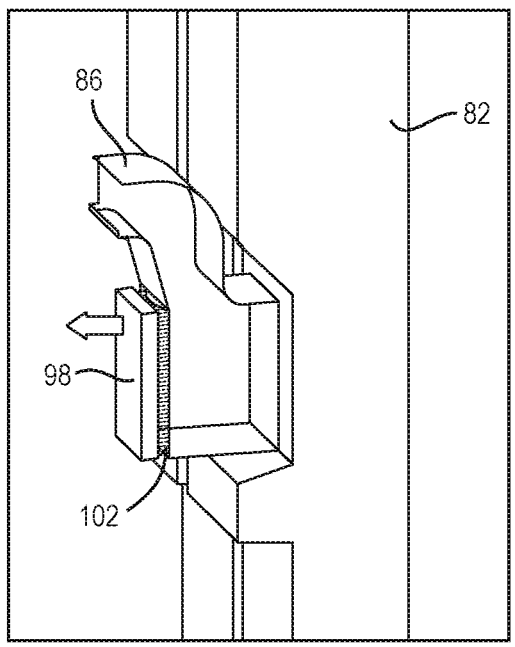

At step 130, the sliding door 106 of the pneumatic delivery terminal 82 is opened to receive the filled prescription 94 (see FIG. 13B). At step 134, the pushing member 98 is operated, using the actuator 110, 114, to transfer the filled prescription 94 from the chute 86 to the pneumatic delivery terminal 82 (see FIG. 13C). As described above, the pushing member 98 may be operated by the ram 110 and the motor 114 to push the prescription from the chute 86 into the pneumatic delivery terminal 82. The electronic processor 111 determines that the door 106 is opened based on communicating, via the transceiver 113, with the pneumatic delivery terminal 82 or the customer kiosk 46, 50, 54 connected to the pneumatic delivery terminal 82. The electronic processor 111 actuates, using the actuator 110, 114, the pushing member 98 to transfer the filled prescription 94 from the chute 86 to the pneumatic delivery terminal 82 in response to determining that the door 106 is opened. The prescription 94 may be transferred to a container within the pneumatic delivery terminal 82.

At step 138, the sliding door 106 is closed. As described above, the sliding door 106 may be closed while the pushing member 98 is still covering the opening to the pneumatic delivery terminal 82. In some embodiments, the sliding door 106 may be closed after the pushing member 98 is returned to its original position.

At step 142, the pushing member 98 is returned to its original position (see FIG. 13D). As described above, the motor 114 and the ram 110 may be controlled by the electronic processor 111 to return the pushing member 98 to its original position. The electronic processor 111 determines that the door 106 is closed based on communicating, via the transceiver 113, with the pneumatic delivery terminal 82 or the customer kiosk 46, 50, 54 connected to the pneumatic delivery terminal 82. The electronic processor 111 actuates, using the actuator (110, 114), the pushing member 98 to retract to the second portion 88 in response to determining that the door 106 is closed. At step 146, the pneumatic delivery terminal 82 delivers the prescription to the appropriate customer kiosk 46, 50, 54 via the respective pneumatic tube 66, 70, 74.

FIG. 15 illustrates one example method 118 of dispensing orders. In other embodiments, the method 118 may perform more or fewer steps than described herein. In addition, the steps of the method 118 may be performed in a different order than described herein.

The method 118 is repeated for other customer kiosks 46, 50, 54 in the pharmacy 10. For example, the method 118 includes receiving, at the pharmaceutical storage and retrieval device 18, a second instruction to deliver a second filled prescription 94 to a second customer kiosk 54 located outside the pharmacy 10. The method 118 includes transferring, using the gantry assembly 90, the second filled prescription 94 to a second chute 86 connecting the pharmaceutical storage and retrieval device 18 and a second pneumatic delivery terminal 82 and opening a second door 106 of the second pneumatic delivery terminal 82. The method 118 further includes operating, using a second actuator 110, 114, a second pushing member 98 positioned in the second chute 86. The second pushing member 98 transfers the second filled prescription 94 from the second chute 86 to the second pneumatic delivery terminal 82. The method 118 also includes closing the second door 106 of the second pneumatic delivery terminal 82 and delivering, via a second pneumatic tube 74, the second filled prescription 94 to the second customer kiosk 54.

Thus, the invention provides, among other things, a system and method for dispensing orders. Various features and advantages of the invention are set forth in the following claims.

What is claimed is:

1. A pharmaceutical storage and retrieval device comprising:
   a housing;
   a storage area in the housing for storing filled prescriptions;
   an outlet on the housing;
   a gantry assembly in the housing configured to transport the filled prescriptions from the storage area to the outlet;
   a chute connecting the outlet to a pneumatic delivery terminal, the chute including:
      a pushing member movable relative to the chute to deliver the filled prescriptions from the chute to the pneumatic delivery terminal, wherein the pushing member includes flexible bristles on a side facing the pneumatic delivery terminal, and
      an actuator coupled to the pushing member and configured to move the pushing member.

2. The pharmaceutical storage and retrieval device of claim 1, wherein the actuator further comprises:
   a ram coupled to the pushing member and configured to move the pushing member, and
   a motor coupled to the ram and configured to actuate the ram.

3. The pharmaceutical storage and retrieval device of claim 1, wherein the chute further includes:
   a first portion coupled to the outlet,
   a second portion including the pushing member, and
   a third portion coupled to an opening in the pneumatic delivery terminal, wherein a door is provided at the opening to open and close the opening.

4. The pharmaceutical storage and retrieval device of claim 3, wherein the gantry assembly transports a first filled prescription from the filled prescriptions to the first portion at the outlet, wherein the first filled prescription moves from the first portion to the second portion, and wherein the pushing member moves the first filled prescription from the second portion into the opening.

5. The pharmaceutical storage and retrieval device of claim 4, wherein the chute is sloped from the first portion to the second portion such that the first filled prescription moves from the first portion to the second portion due to gravity.

6. The pharmaceutical storage and retrieval device of claim 4, wherein the first filled prescription includes a first magnet and the second portion includes a second magnet such that the first filled prescription moves from the first portion to the second portion due to a magnetic field created between the first magnet and the second magnet.

7. The pharmaceutical storage and retrieval device of claim 4, wherein the first filled prescription includes a magnet and the second portion creates a magnetic field such that the first filled prescription moves from the first portion to the second portion due to the magnetic field acting on the magnet.

8. The pharmaceutical storage and retrieval device of claim 4, wherein the pushing member is shaped to substantially cover the opening when the pushing member transports the first filled prescription to the opening.

9. The pharmaceutical storage and retrieval device of claim 4, wherein the pushing member remains at the opening after transporting the first filled prescription to the opening until the door closes the opening.

10. The pharmaceutical storage and retrieval device of claim 4, further comprising:
    a transceiver for communicating with the pneumatic delivery terminal; and
    an electronic processor coupled to the transceiver and configured to:
       receive, via the transceiver, an instruction to deliver a filled prescription to a customer kiosk,
       control the gantry assembly to transport the filled prescription from the storage area to the chute, and
       operate, using the actuator, the pushing member to transfer the filled prescription from the chute to the pneumatic delivery terminal.

11. The pharmaceutical storage and retrieval device of claim 10, wherein the electronic processor is further configured to determine that the door is opened, wherein the pushing member is operated to transfer the filled prescription from the chute to the pneumatic delivery terminal in response to determining that the door is opened.

12. The pharmaceutical storage and retrieval device of claim 10, wherein the electronic processor is further configured to:
    determine that the door is closed, and
    operate the pushing member to retract to the second portion in response to determining that the door is closed.

13. The pharmaceutical storage and retrieval device of claim 1, wherein the flexible bristles have a concave profile.

14. The pharmaceutical storage and retrieval device of claim 3, wherein the door is a sliding door, wherein the bristles are configured to deflect out of the way of the sliding door and are not trapped in the sliding door when the sliding door is closed.

15. The pharmaceutical storage and retrieval device of claim 1, wherein the pushing member is moved horizontally and laterally between the chute and the pneumatic delivery terminal by the actuator.

16. The pharmaceutical storage and retrieval device of claim 15, wherein the pushing member is configured to transport a plurality of containers carrying the filled prescriptions to the pneumatic delivery terminal at the same time.

17. A pharmacy dispensing system comprising:
    a pharmaceutical storage and retrieval device inside a pharmacy, the pharmaceutical storage and retrieval device including a first outlet and a second outlet;
    a first kiosk located inside the pharmacy;
    a second kiosk located outside the pharmacy;
    a pneumatic delivery system connecting the pharmaceutical storage and retrieval device, the first kiosk, and the second kiosk, the pneumatic delivery system including
       a first pneumatic delivery terminal coupled to the first outlet,
       a first pneumatic delivery conduit extending between the first pneumatic delivery terminal to the first kiosk, wherein filled prescriptions are delivered from the first outlet to the first kiosk through the first pneumatic delivery terminal and the first pneumatic delivery conduit,
       a second pneumatic delivery terminal coupled to the second outlet, and
       a second pneumatic delivery conduit extending between the second pneumatic delivery terminal to the second kiosk, wherein filled prescriptions are delivered from the second outlet to the second kiosk through the second pneumatic delivery terminal and the second pneumatic delivery conduit;
a gantry assembly in a housing of the pharmaceutical storage and retrieval device, the gantry assembly configured to transport the filled prescriptions to the first outlet and the second outlet; and
a chute connecting the first outlet to the first pneumatic delivery terminal, the chute including:
  a pushing member movable relative to the chute to deliver the filled prescriptions from the chute to the first pneumatic delivery terminal,
  an actuator coupled to the pushing member and configured to move the pushing member,
  a first portion coupled to the first outlet,
  a second portion including the pushing member, and
  a third portion coupled to an opening in the first pneumatic delivery terminal,
wherein a door is provided by the opening to open and close the opening,
wherein the gantry assembly transports a first filled prescription from the filled prescriptions to the first portion at the first outlet, wherein the first filled prescription moves from the first portion to the second portion, and wherein the pushing member moves the first filled prescription from the second portion into the opening;
a transceiver for communicating with the pneumatic delivery system; and
an electronic processor coupled to the transceiver and configured to
  receive, via the transceiver, an instruction to deliver a filled prescription to the first kiosk,
  control the gantry assembly to transport the filled prescription to the chute,
  operate, using the actuator, the pushing member to transfer the filled prescription from the chute to the first pneumatic delivery terminal,
  determine that the door is closed, and
  operate the pushing member to retract to the second portion in response to determining that the door is closed.

18. The pharmacy dispensing system of claim 17, wherein the actuator further comprises:
  a ram coupled to the pushing member and configured to move the pushing member, and
  a motor coupled to the ram and configured to actuate the ram.

19. The pharmacy dispensing system of claim 17, wherein the chute is sloped from the first portion to the second portion such that the first filled prescription moves from the first portion to the second portion due to gravity.

20. The pharmacy dispensing system of claim 17, wherein the first filled prescription includes a first magnet and the second portion includes a second magnet such that the first filled prescription moves from the first portion to the second portion due to a magnetic field created between the first magnet and the second magnet.

21. The pharmacy dispensing system of claim 17, wherein the first filled prescription includes a magnet and the second portion creates a magnetic field such that the first filled prescription moves from the first portion to the second portion due to the magnetic field acting on the magnet.

22. The pharmacy dispensing system of claim 17, wherein the pushing member includes flexible bristles on a side facing the first pneumatic delivery terminal.

23. The pharmacy dispensing system of claim 22, wherein the flexible bristles have a concave profile.

24. The pharmacy dispensing system of claim 17, wherein the pushing member is shaped to substantially cover the opening when the pushing member transports the first filled prescription to the opening.

25. The pharmacy dispensing system of claim 17, wherein the pushing member remains at the opening after transporting the first filled prescription to the opening until the door closes the opening.

26. The pharmacy dispensing system of claim 17, wherein the electronic processor is further configured to determine that the door is opened, wherein the pushing member is operated to transfer the filled prescription from the chute to the first pneumatic delivery terminal in response to determining that the door is opened.

27. A method for dispensing orders, comprising:
  receiving, at a pharmaceutical storage and retrieval device, an instruction to deliver a filled prescription to a customer kiosk;
  transferring, using a gantry assembly, the filled prescription to a chute connecting the pharmaceutical storage and retrieval device and a pneumatic delivery terminal;
  opening a door of the pneumatic delivery terminal;
  operating an actuator to transfer the filled prescription from the chute to the pneumatic delivery terminal, wherein operating the actuator further comprises:
    determining that the door is opened, and
    actuating the actuator to transfer the filled prescription from the chute to the pneumatic delivery terminal in response to determining that the door is opened;
  closing the door of the pneumatic delivery terminal;
  delivering, via a pneumatic tube, the filled prescription to the customer kiosk;
  determining that the door is closed; and
  actuating the actuator to retract in response to determining that the door is closed.

28. The method of claim 27, wherein the customer kiosk is located inside a pharmacy, the method further comprising:
  receiving, at the pharmaceutical storage and retrieval device, a second instruction to deliver a second filled prescription to a second customer kiosk located outside the pharmacy;
  transferring, using the gantry assembly, the second filled prescription to a second chute connecting the pharmaceutical storage and retrieval device and a second pneumatic delivery terminal;
  opening a second door of the second pneumatic delivery terminal;
  operating a second actuator to transfer the second filled prescription from the second chute to the second pneumatic delivery terminal;
  closing the second door of the second pneumatic delivery terminal; and
  delivering, via a second pneumatic tube, the second filled prescription to the second customer kiosk.

29. The method of claim 27, wherein the actuator includes a motor coupled to a pushing member, wherein operating the actuator further comprises controlling the motor to move the pushing member.

30. The method of claim 29, wherein transferring the filled prescription to the chute further comprises transporting, using the gantry assembly, the filled prescription from a storage area of the pharmaceutical storage and retrieval device to a first portion of the chute at an outlet of the pharmaceutical storage and retrieval device.

31. The method of claim 30, further comprising:
moving the filled prescription from the first portion to a second portion of the chute, wherein actuating the actuator includes moving the filled prescription from the second portion into an opening of the pneumatic delivery terminal.

32. The method of claim 31, further comprising:
substantially covering, using the pushing member, the opening when the pushing member transports the filled prescription to the opening.

\* \* \* \* \*